United States Patent [19]

Kwon et al.

[11] Patent Number: 5,723,702
[45] Date of Patent: Mar. 3, 1998

[54] METHOD FOR REMOVING MOISTURE FROM CHLORODIFLUORO-METHANE

[75] Inventors: Young Soo Kwon; Kun You Park; Sang-Deuk Lee; Honggon Kim, all of Seoul, Rep. of Korea

[73] Assignee: Korea Institute of Science and Technology, Seoul, Rep. of Korea

[21] Appl. No.: 615,092

[22] Filed: Mar. 13, 1996

Related U.S. Application Data

[63] Continuation-in-part of Ser. No. 347,803, Nov. 30, 1994, abandoned.

[30] Foreign Application Priority Data

Dec. 9, 1993 [KR] Rep. of Korea ............... 27090/1993

[51] Int. Cl.$^6$ ............................................. C07C 17/38
[52] U.S. Cl. ............................................. 570/177
[58] Field of Search ............................................. 570/172

[56] References Cited

FOREIGN PATENT DOCUMENTS

| 50-12405 | 5/1975 | Japan | 570/177 |
| 1401541 | 7/1975 | United Kingdom | 570/177 |

OTHER PUBLICATIONS

Weissberger Separation and Purification Part 1, 2nd Ed. pp. 809, 816 (1956).

*Encyclopedia of Chemical Technology*, 3rd ed., 4:433, John Wiley & Sons (1984).

T.A. Wittstruck et al., "Some Hydrates of Some Halomethanes," *J. Chem. Eng. Data*, 6(3):343–346 (1961).

*Primary Examiner*—Alan Siegel
*Attorney, Agent, or Firm*—Darby & Darby

[57] ABSTRACT

There is a process for removing moisture from chlorodifluoromethane ($CHClF_2$) containing moisture in excess in the preparation of chlorodifluoromethane comprising lowering the partial pressure of water in the chlorodifluoromethane gas by contacting the chlorodifluoromethane gas with an aqueous solution of calcium chloride of more than 5% by weight.

9 Claims, 1 Drawing Sheet

METHOD FOR REMOVING MOISTURE FROM CHLORODIFLUORO-METHANE

This application is a continuation-in-part of U.S. Ser. No. 08/347,803, filed Nov. 30, 1994 now abandoned.

BACKGROUND OF THE INVENTION

1. Field of the Invention

The present invention relates to a process for removing moisture from chlorodifluoromethane ($CHClF_2$) gas in the preparation of chlorodifluoromethane. More particularly, the present invention relates to a process for removing moisture from chlorodifluoromethane gas containing moisture in excess by contacting the chlorodifluoromethane gas with an aqueous solution of calcium chloride.

2. Description of the Prior Art

Chlorodifluoromethane, used as a refrigerant, may be produced by reaction of chloroform ($CHCl_3$) with hydrogen fluoride (HF) in the presence of a catalyst such as pentachloroantimony ($SbCl_5$). The product of the reaction contains not only chlorodifluoromethane but also by-products such as hydrogen chloride (HCl) and high boilers, unreacted HF, etc. HCl, unreacted HF and high boilers can be relatively easily separated from chlorodifluoromethane by distillation, absorption and layer separation. Meanwhile, a small quantity of acids remaining in chlorodifluoromethane can be removed by washing chlorodifluoromethane with water or aqueous alkali solution. However, after this washing, chlorodifluoromethane is saturated with water.

The content of moisture in chlorodifluoromethane which can be used as a refrigerant is desirably less than 20 ppm. Therefore, to be capable of being a refrigerant, the moisture content of chlorodifluoromethane should be lowered.

Several known methods can be applied to remove moisture from chlorodifluoromethane: adsorption, absorption using cold water, absorption using concentrated sulfuric acid, and condensation, etc.

Adsorption method in which solid adsorbents such as molecular sieve, silica gel, anhydrous calcium chloride or alumina are used as water adsorbents is useful for the case that chlorodifluoromethane contains relatively little amount of moisture. When a large amount of moisture is contained in chlorodifluoromethane, the adsorbent has to be regenerated too frequently, which makes the overall procedure for moisture removing complicated and the operation cost high. Therefore, a preliminary drying process such as absorption or condensation is required to remove the large mount of moisture prior to the adsorption method.

In cold water absorption method ususally used as a preliminary drying process, moisture in chlorodifluoromethane gas is removed by directly contacting the chlorodifluoromethane gas with cold water slightly above the freezing point, for example at about 5° C., to reduce the partial pressure of water in chlorodifluoromethane gas and condense the moisture from the gas. The higher the pressure and the lower the temperature of the absorption process, the more efficient the moisture removal is. However, at a condition of high pressure and low temperature, chlorodifluoromethane is apt to form hydrate with water, resulting in the loss of chlorodifluoromethane (refer to table 1, recited from *J. of Chem. and Eng. Data*, Vol. 6, No. 3, pp 343–346, 1961). Therefore, the operating temperature in this method has to be kept at least above the temperature where the water is frozen and chlorodifluoro-methane hydrate is formed. In addition, the operating pressure should be maintained below the pressure where the chlorodifluoromethane gas is liquified. These limitations of operating conditions cause insufficiency in removal of moisture.

TABLE 1

| chlorodifluoromethane hydrate formation temp. | |
|---|---|
| pressure ($kg/cm^2$-g) | hydrate formation temp. (°C.) |
| 6.0 | 15.7 |
| 3.0 | 11.5 |
| 1.0 | 6.2 |
| atmospheric pressure | 1.0 |

In sulfuric acid absorption method, highly concentrated sulfuric acid is used as an absorbent for removal of moisture. In this method, the absorption equipment is subject to corrosion caused by the sulfuric acid. In addition, the regeneration process should be so complicate and expensive that it is impractical to concentrate the sulfuric acid diluted by absorbing moisture from the chlorodifluoromethane.

In the condensing method, chlorodifluoromethane gas is cooled in a condenser in order to condense moisture. In this method, very low temperature is required in order to remove moisture efficiently from the chlorodifluoromethane gas. However, at low temperature, chlorodifluoromethane forms hydrate with water and the hydrate adheres to the interior of the equipment. Though the hydrate may be removed by heating, the loss of chlorodifluoromethane due to hydrate formation can not be avoided.

SUMMARY OF THE INVENTION

The object of the present invention is to provide a process for removing moisture from chlorodifluoromethane containing moisture in excess. In accordance with the present process, the efficiency of moisture removal is improved and the loss of chlorodifluoromethane is almost eliminated.

The present process can be used as a preliminary procedure, which can efficiently remove a large quantity of moisture such as more than 1000 ppm prior to a method which is proper for removing a small quantity of moisture such as less than 500 ppm in chlorodifluoromethane.

In the process according to the present invention, the moisture contained in chlorodifluoromethane gas is removed efficiently by contacting the gas with an aqueous calcium chloride solution. In addition, almost all of the chlorodifluoromethane dissolved in the aqueous calcium chloride solution is easily recovered without thermal decomposition, and the diluted calcium chloride solution is also easily regenerated in a separate stage and used continuously. Therefore, in accordance with the present invention, the moisture content of chlorodifluoromethane can be lowered, and the loss of chlorodifluoromethane can be minimized.

DETAILED DESCRIPTION OF THE INVENTION

Figure 1:
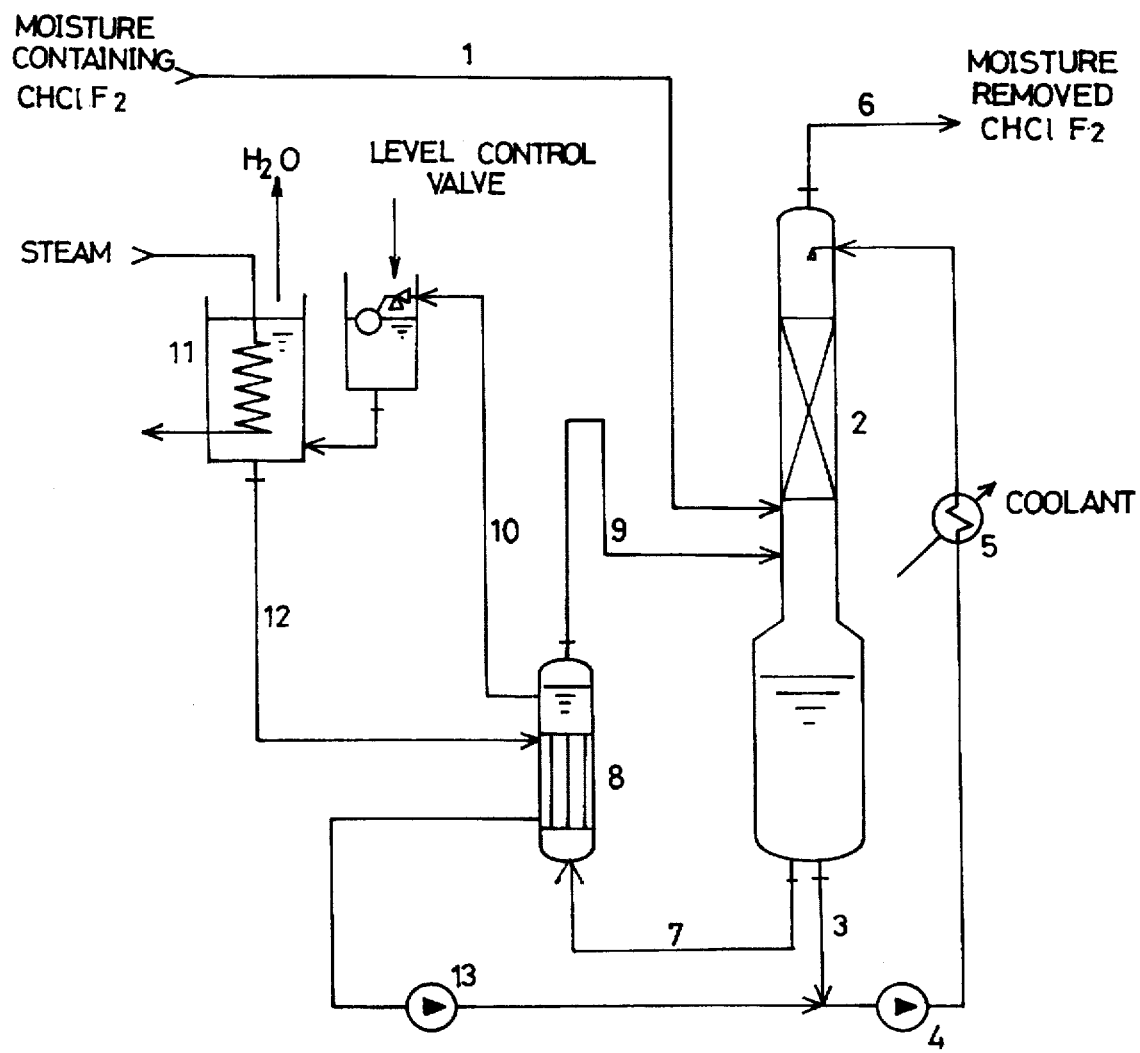
FIG. 1 is an example of a scheme of the process according to the present invention.

According to the present invention, for removing moisture from chlorodifluoromethane gas containing moisture in excess, the chiorodifluoromethane gas is contacted with an aqueous calcium chloride solution of more than 5% by weight, preferably more than 30% by weight. By contacting the chlorodifluoromethane gas with the calcium chloride solution, the partial pressure of water in the chlorodifluoromethane gas is lowered, and thus the moisture in the chlorodifluoromethane gas is condensed as water.

A little chlorodifluoromethane dissolved in the calcium chloride solution during the process of moisture removal can be recovered by heating the diluted calcium chloride solution at a temperature above 30° C., preferably above 50° C.

When calcium chloride solution of 30% by weight is used as an absorbent instead of water, the partial pressure of water is lowered to about 60% compared to that of pure water. Therefore, at the same temperature, much larger mount of moisture can be removed from chlorodifluoromethane gas when contacting the gas with a calcium chloride solution than with water.

Since the freezing point of calcium chloride solution can be far lower than 0° C., it is also possible to further reduce the partial pressure of water in the gas at an operating temperature below 0° C.

In addition, in the calcium chloride solution, the range of temperature where chlorodifluoromethane hydrate may be formed is narrowed. For example, when calcium chloride solution of 30% by weight is used, chlorodifluoromethane hydrate is not formed under the conditions that the temperature is above −10° C. and the pressure is below the vapor pressure of chlorodifluoromethane at the operating temperature. Therefore, formation of chlorodifluoromethane hydrate can be avoided in broad operation conditions.

When compared to the sulfuric acid absorption method, the present invention using calcium chloride solution eliminates corrosion of equipment due to the use of a corrosive solution.

After moisture absorption, the diluted calcium chloride solution is easily regenerated by a simple process using a heat exchanger and concentrating equipment. A small quantity of chlorodifluoromethane dissolved in the calcium chloride solution can be continuously recovered without thermal decomposition, for example in a heat exchanger, at a temperature above 30° C., more preferably above 50° C. Thereafter the diluted calcium chloride solution is regenerated by heating at a temperature above 70° C., more preferable above 100° C. in the concentrating equipment. For absorbing the moisture using calcium chloride solution, a packed tower, a spray tower or a plate tower can be used as the absorption equipment The present invention is illustrated in more detail by referring to the attached drawing.

Chlorodifluoromethane gas containing moisture in excess is supplied to the bottom of an absorption tower 2. To the upper part of the absorption tower, aqueous calcium chloride solution is supplied. The chlorodifluoromethane gas is contacted with the calcium chloride solution in countercurrent while it passes through the packing material in the absorption tower. After then, the chlorodifluoromethane gas which has lower moisture content is drawn off from the upper part of the tower and the calcium chloride solution diluted by moisture condensed from the moisture containing chlorodifluoromethane gas is drawn off from the lower part of the tower.

A little amount of chlorodifluoromethane may be dissolved in the diluted calcium chloride solution. It is recovered from the solution, for example in a heat exchanger, at a mild temperature before the diluted calcium chloride solution is regenerated.

Calcium chloride solution which has almost no chlorodifluoromethane can be easily regenerated in such a simple method that the diluted solution is heated, for example with steam, in a concentrator 11. The water in the diluted calcium chloride solution is evaporated and removed, and the solution is regenerated to the initial concentration of calcium chloride. The recovered chlorodifluoromethane gas and the regenerated calcium chloride solution are resupplied to the absorption tower, respectively.

Operation conditions are not specially limited if formation of chlorodifluoromethane hydrate can be avoided. However, higher operating pressure and lower operating temperature are desirable.

Other features, advantages and embodiments of the invention disclosed herein will be readily apparent to those exercising ordinary skill in the art after reading the foregoing disclosures. In this regard, while specific embodiments of the invention have been described in considerable detail, variations and modifications of these embodiments can be effected without departing from the spirit and scope of the invention as described and claimed.

EXAMPLE 1.

Chlorodifluoromethane gas containing 6000 ppm of water was supplied to the bottom of an absorption tower 2 packed with pall-ring, at a rate of 100 kg/hr. To the upper part of the absorption tower, 30% by weight of calcium chloride aqueous solution was supplied. The operation conditions of the absorption tower were as follows: temperature: 5° C., pressure: 3.0 kg/cm$^2$-g, circulating rate of calcium chloride solution: 1000 kg/hr. From the lower part of the tower the diluted calcium chloride solution was drawn off and transferred to a heat exchanger 8 in which the solution was heated with the regenerated calcium chloride solution from a concentrator 11. The chlorodifluoromethane dissolved in the diluted calcium chloride solution was recovered as gas in the heat exchanger 8 and resupplied to the tower 2 via pipe 9. The diluted calcium chloride solution was transferred into the concentrator 11 to concentrate the solution. The regenerated calcium chloride solution in the concentrator 11 was transferred into the heat exchanger 8 through a pipe 12. The regenerated solution was passed through a pump 13 and circulation pump 4, and cooled in a cooler 5. After cooling, the solution was resupplied to the absorption tower 2.

After 10 hrs. the process reached a steady state. Moisture content of the chlorodifluoromethane gas from the upper part of the absorption tower was 300 ppm. In the circulation solution, chlorodifluoromethane hydrate was not detected.

COMPARATIVE EXAMPLE.

Chlorodifluoromethane containing moisture was treated in a manner similar to that of Example 1, except that water was used instead of calcium chloride solution. After 10 hours, moisture content of the chlorodifluoromethane gas from the upper part of the absorption tower was 480 ppm. In the circulation solution, an appreciable mount of chlorodifluoromethane hydrate was detected, and parts of the hydrate adhered to the interior of the tower.

EXAMPLE 2.

Chlorodifluoromethane was treated in a manner similar to that of Example 1, except that the operation temperature was −5° C. instead of 5° C. Moisture content of the chlorodifluoromethane gas from the upper part of the absorption tower was 140 ppm after 10 hours operation. In the circulation solution, chlorodifluoromethane hydrate was not detected.

What is claimed is:

1. A process for removing moisture from chlorodifluoromethane ($CHClF_2$) containing moisture in excess comprising the steps of:
   (a) lowering the partial pressure of water in the chlorodifluoromethane gas by contacting the chlorodifluoromethane gas with an aqueous solution of calcium chloride of more than 5% by weight;
   (b) recovering chlorodifluoromethane dissolved in the used aqueous solution of calcium chloride at a temperature above 30° C. before regenerating the used calcium chloride solution; and
   (c) regenerating said used calcium chloride solution by heating the calcium chloride solution at a temperature above 70° C.

2. The process in accordance with claim 1, wherein the concentration of the aqueous solution of calcium chloride is from 20% to 40% by weight.

3. The process in accordance with claim 1, wherein the contacting the chlorodifluoromethane gas with the aqueous solution of calcium chloride in step (a) is taken place in an equipment selected from a group consisting of a packed tower, a spray tower and a plate tower.

4. The process in accordance with claim 1, wherein the contacting the chlorodifluoromethane gas with the aqueous solution of calcium chloride in step (a) is taken place under the conditions of a low temperature above the freezing point of said calcium chloride solution and of a pressure below the vapor pressure of chlorodifluoromethane at the operating temperature.

5. The process in accordance with claim 1, wherein the recovering step (b) is carried out in a heat exchanger at a temperature of from 50° C. to 100° C. and the recovered chlorodifluoromethane is recycled to the contacting step (a).

6. The process in accordance with claim 1, wherein the regenerating step (c) is carried out at a temperature above 100° C.

7. The process in accordance with claim 1, wherein the regenerated calcium chloride solution is recycled to the step (a).

8. The process in accordance with claim 5, wherein the regenerated calcium chloride solution is recycled to the step (a).

9. The process in accordance with claim 8, wherein the regenerated calcium chloride solution is passed through the heat exchanger before it is recycled to the step (a).

* * * * *